(12) United States Patent
McLaughlin et al.

(10) Patent No.: US 7,361,514 B2
(45) Date of Patent: Apr. 22, 2008

(54) SYSTEM AND METHOD FOR GAS DISCHARGE SPECTROSCOPY

(75) Inventors: James McLaughlin, Belfast (GB); Paul Damian Maguire, Belfast (GB)

(73) Assignee: UUTech Limited, County Antrim (GB)

( * ) Notice: Subject to any disclaimer, the term of this patent is extended or adjusted under 35 U.S.C. 154(b) by 865 days.

(21) Appl. No.: 10/433,026

(22) PCT Filed: Nov. 29, 2001

(86) PCT No.: PCT/GB01/05290

§ 371 (c)(1), (2), (4) Date: Dec. 5, 2003

(87) PCT Pub. No.: WO02/44698

PCT Pub. Date: Jun. 6, 2002

(65) Prior Publication Data

US 2004/0106213 A1 Jun. 3, 2004

(30) Foreign Application Priority Data

Nov. 30, 2000 (GB) ................................. 0029218.5

(51) Int. Cl.
*G01N 21/00* (2006.01)
*B32B 21/00* (2006.01)

(52) U.S. Cl. .................. 436/164; 436/172; 422/82.05; 422/82.08; 422/83

(58) Field of Classification Search .................... None
See application file for complete search history.

(56) References Cited

U.S. PATENT DOCUMENTS 3,798,501 A 3/1974 Miller
5,085,499 A * 2/1992 Griffin et al. ................ 356/311

FOREIGN PATENT DOCUMENTS

GB 2 344 212 A 5/2000

OTHER PUBLICATIONS

International Search Report for PCT/GB01/05290.

* cited by examiner

*Primary Examiner*—Yelena G. Gakh
(74) *Attorney, Agent, or Firm*—Drinker Biddle & Reath LLP

(57) ABSTRACT

A system for identifying gases, the system having a plasma generator for generating a plasma using the gas to be identified and an array of detectors for detecting light emitted from the plasma. By analysing the output of the detectors, the gas can be identified. The system includes a plasma display (11) having two glass plates (36 and 38) patterned with strips that form the plasma electrodes. The intersection between the strips defines pixels which are individually addressable.

20 Claims, 8 Drawing Sheets

| Air Samples | | | |
|---|---|---|---|
| 1 | 0 | 0.997695 | 0.002251 |
| 1 | 0 | 0.997683 | 0.002264 |
| 1 | 0 | 0.997683 | 0.002264 |
| 1 | 0 | 0.997683 | 0.002264 |
| 1 | 0 | 0.997683 | 0.002264 |
| Nitrogen Samples | | | |
| 0 | 1 | 0.002174 | 0.997885 |
| 0 | 1 | 0.00217 | 0.99789 |
| 0 | 1 | 0.00217 | 0.99789 |
| 0 | 1 | 0.002169 | 0.99789 |
| 0 | 1 | 0.00217 | 0.99789 |

| Desired Output | | | ActualOutput | | |
|---|---|---|---|---|---|
| Air Samples | | | | | |
| 1 | 0 | 0 | 0.955491 | 0.000574 | 0.052029 |
| 1 | 0 | 0 | 0.1904 | 0.000327 | 0.85308 |
| 1 | 0 | 0 | 0.000737 | 0.000432 | 0.998846 |
| 1 | 0 | 0 | 0.998666 | 0.001583 | 0.000843 |
| 1 | 0 | 0 | 0.996318 | 0.000818 | 0.003911 |
| Acetone Samples | | | | | |
| 0 | 1 | 0 | 0.000851 | 0.998787 | 0.00056 |
| 0 | 1 | 0 | 0.001083 | 0.998782 | 0.000454 |
| 0 | 1 | 0 | 0.001083 | 0.998782 | 0.000454 |
| 0 | 1 | 0 | 0.00088 | 0.998785 | 0.000544 |
| 0 | 1 | 0 | 0.001083 | 0.998782 | 0.000454 |
| Vinegar Samples | | | | | |
| 0 | 0 | 1 | 0.00065 | 0.000467 | 0.998888 |
| 0 | 0 | 1 | 0.000747 | 0.000434 | 0.998828 |
| 0 | 0 | 1 | 0.00058 | 0.00048 | 0.99897 |
| 0 | 0 | 1 | 0.000655 | 0.000448 | 0.998925 |
| 0 | 0 | 1 | 0.000747 | 0.000434 | 0.998828 |

*Fig. 5*

| Desired Output | | | ActualOutput | | |
|---|---|---|---|---|---|
| Air Samples | | | | | |
| 1 | 0 | 0 | 0.809178 | 0.000113 | 0.210654 |
| 1 | 0 | 0 | 0.456088 | 0.000277 | 0.690508 |
| 1 | 0 | 0 | 0.001086 | 0.000381 | 0.999267 |
| 1 | 0 | 0 | 0.998054 | 0.001476 | 0.001158 |
| 1 | 0 | 0 | 0.981448 | 0.000071 | 0.029452 |
| Acetone Samples | | | | | |
| 0 | 1 | 0 | 0.000549 | 0.999483 | 0.000606 |
| 0 | 1 | 0 | 0.000891 | 0.99952 | 0.000583 |
| 0 | 1 | 0 | 0.000891 | 0.99952 | 0.000583 |
| 0 | 1 | 0 | 0.000542 | 0.999462 | 0.000612 |
| 0 | 1 | 0 | 0.000891 | 0.99952 | 0.000583 |
| Vinegar Samples | | | | | |
| 0 | 0 | 1 | 0.001427 | 0.000408 | 0.998891 |
| 0 | 0 | 1 | 0.002317 | 0.00044 | 0.998847 |
| 0 | 0 | 1 | 0.000635 | 0.00037 | 0.999322 |
| 0 | 0 | 1 | 0.001032 | 0.000399 | 0.999295 |
| 0 | 0 | 1 | 0.002317 | 0.00044 | 0.998847 |

*Fig. 6*

| Desired Output | | | ActualOutput | | |
|---|---|---|---|---|---|
| Air Samples | | | | | |
| 0 | 0 | 1 | 0.203246 | 0.422647 | 0.008557 |
| 0 | 1 | 0 | 0.043378 | 0.966702 | 0.000695 |
| 1 | 0 | 0 | 0.834635 | 0.038629 | 0.084081 |
| 0 | 0 | 1 | 0.356312 | 0.137691 | 0.51315 |
| 0 | 1 | 0 | 0.312814 | 0.743232 | 0.004131 |
| 1 | 0 | 0 | 0.356312 | 0.137691 | 0.51315 |
| 0 | 0 | 1 | 0.087877 | 0.051717 | 0.940178 |
| 0 | 1 | 0 | 0.026199 | 0.515117 | 0.270183 |
| 1 | 0 | 0 | 0.761601 | 0.24571 | 0.042808 |
| 0 | 0 | 1 | 0.069182 | 0.012151 | 0.930047 |
| Acetone Samples | | | | | |
| 0 | 1 | 0 | 0.005161 | 0.521229 | 0.467571 |
| 1 | 0 | 0 | 0.981986 | 0.017954 | 0.001605 |
| 0 | 0 | 1 | 0.005161 | 0.521229 | 0.467571 |
| 0 | 1 | 0 | 0.017027 | 0.938611 | 0.090301 |
| 1 | 0 | 0 | 0.964254 | 0.000536 | 0.06373 |
| 0 | 0 | 1 | 0.00749 | 0.084674 | 0.909185 |
| 0 | 1 | 0 | 0.009131 | 0.897328 | 0.097647 |
| 1 | 0 | 0 | 0.972448 | 0.010791 | 0.005032 |
| 0 | 0 | 1 | 0.023653 | 0.019436 | 0.956679 |
| 0 | 1 | 0 | 0.023992 | 0.984851 | 0.002682 |
| Vinegar samples | | | | | |
| 1 | 0 | 0 | 0.781438 | 0.064721 | 0.056965 |
| 0 | 0 | 1 | 0.27383 | 0.091259 | 0.721532 |
| 0 | 1 | 0 | 0.0132 | 0.788827 | 0.119293 |
| 1 | 0 | 0 | 0.00741 | 0.630546 | 0.20925 |
| 0 | 0 | 1 | 0.266669 | 0.169228 | 0.725187 |
| 0 | 1 | 0 | 0.138254 | 0.328611 | 0.113154 |
| 1 | 0 | 0 | 0.732179 | 0.16889 | 0.288694 |
| 0 | 0 | 1 | 0.112854 | 0.414721 | 0.45704 |
| 0 | 1 | 0 | 0.112854 | 0.414721 | 0.45704 |
| 1 | 0 | 0 | 0.983031 | 0.035649 | 0.023203 |

*Fig. 7*

| Desired Output | | ActualOutput | |
|---|---|---|---|
| sample A | | | |
| 1 | 0 | 0.992473 | 0.007436 |
| 1 | 0 | 0.99547 | 0.004413 |
| sample B | | | |
| 0 | 1 | 0.992473 | 0.007436 |
| 0 | 1 | 0.995607 | 0.004261 |

*Fig. 8*

| Desired Output | | ActualOutput | |
|---|---|---|---|
| sample A | | | |
| 1 | 0 | 0.999381 | 0.000611 |
| 1 | 0 | 0.999853 | 0.000143 |
| 1 | 0 | 0.999687 | 0.000307 |
| 1 | 0 | 0.999381 | 0.000611 |
| 1 | 0 | 0.802243 | 0.198052 |
| sample B | | | |
| 0 | 1 | 0.085314 | 0.914361 |
| 0 | 1 | 0.000289 | 0.999725 |
| 0 | 1 | 0.999099 | 0.000893 |
| 0 | 1 | 0.000391 | 0.999625 |
| 0 | 1 | 0.000292 | 0.999722 |

*Fig. 9*

SYSTEM AND METHOD FOR GAS DISCHARGE SPECTROSCOPY

The present invention relates to improvements in gas discharge spectroscopy.

In the last few years there has been increasing interest in artificial olfaction applications, also termed "artificial nose applications". The purpose of these applications is to try to associate a gas sample with some form of label. Many commercial applications are available for doing this, which uses a variety of different sensors. Electronic nose sensors fall into several different categories: conductivity sensors; piezoelectric sensors; MOSFETS and optical sensors.

There are two types of conductivity sensors that are used for electronic nose applications: metal oxide and polymer, both of which exhibit a change in resistance when exposed to volatile organic compounds (VOC's). Of the two types, metal oxide semiconductors have been used more extensively in electronic nose instruments and are widely available commercially. Typical offerings include oxides of Sn, Zn, Ti, W and Ir, doped with a noble metal catalyst such as palladium or platinum. The doped semiconducting material with which the VOC's interact is deposited between two metal contacts over a resistive heating element, which operates at 200° C. to 400° C. At these elevated temperatures, heat dissipation becomes a major consideration of the mechanical design of the sensing chamber. Micromachining is often used to thin the sensor substrate under the active material, so that power consumption and heat dissipation requirements are reduced. As a VOC passes over the doped oxide material, the resistance between the two metal contacts changes in proportion to the concentration of VOC.

Typically the active metal oxide sensor material is designed to enhance the response to specific odorants, such as carbon monoxide or ammonia. Selectivity can be improved by altering the operating temperature. Sensor sensitivity ranges from 5 to 500 ppm. The sensors also respond to water vapour, more specifically to humidity differences between the gas sample being analysed and a known reference gas used to initialise the sensor.

A disadvantage of metal oxide sensors is that the baseline response is prone to drift over periods of hours to days. To counteract this, signal processing algorithms are usually employed. A further disadvantage is that the sensors are susceptible to poisoning by sulfur compounds present in the odorant mixture. This can cause problems. However, the low cost and wide availability of this type of sensor makes it the most widely used type of gas sensor.

Polymer sensors can also be used as electronic nose conductivity sensors. Here, the active material is a conducting polymer from such families as the polypyrroles, thiophenes, indoles or furans. Changes in the conductivity of these materials occur as they are exposed to various types of chemicals, which bond with the polymer backbone. The bonding may be ionic or covalent. The interaction affects the transfer of electrons along the polymer chain, that is to say, its conductivity. A given compound's affinity for a polymer and its effects on the polymer's conductivity are strongly influenced by the counter-ions and functional groups attached to the polymer backbone.

In order to use polymers in a sensor device, microfabrication techniques are employed to form two electrodes separated by a gap of 10 to 20 μm. Then the conducting polymer is electropolymerized between the electrodes by cycling the voltage between them. For example, layers of polypyrroles can be formed by cycling between −0.7 and +1.4V. Varying the voltage sweep rate and applying a series of polymer precursors yields a wide variety of active materials. Response time is inversely proportional to the polymer thickness. To speed up the response times, micrometer sized conducting polymer bridges are formed between the contact electrodes.

Because conducting polymer sensors operate at ambient temperature, they do not need heaters and thus are easier to make than metal oxide sensors. The electronic interface is straightforward and they are suitable for portable instruments. The sensors can detect odours at sensitivities of 0.1 ppm, but 10 to 100 ppm is more usual. The main drawback of such sensors is that it is difficult and time consuming to electropolymerize the active material, and so they exhibit undesirable variations from one batch to another. Sensor responses also drift over time, and their usually greater sensitivity than metal oxides to water vapour, renders them susceptible to humidity. This susceptibility can mask the responses to odorous volatile organic compounds. In addition, some odorants can penetrate the polymer bulk, thereby prolonging the sensor recovery time by slowing the removal of the VOC from the polymer. This extends the cycle time for sequentially processing odorant samples. This is a disadvantage.

Another group of electronic new sensors currently available is the piexoelectric group. There are two types of sensors, piexoelectric sensors: quartz and crystal microbalance (QCM) and surface acoustic wave (SAW) devices. These sensors can measure temperature, mass changes, pressure, force and acceleration, but in the e-nose applications they are configured as mass change sensing devices.

QCM sensors consist of a resonating disk a few mm in diameter, with metal electrodes on each side connected to a lead wire. The device resonates at a characteristic frequency, typically in the range of 10 MHz to 30 MHz, when excited with an oscillating signal. During manufacture, a polymer coating is applied to the disk to serve as the active sensing material. In operation, a gas sample is absorbed at the surface of the polymer, increasing the mass of the disk-polymer device and thereby reducing the resonance frequency. The reduction is inversely proportional to the odorant mass absorbed by the polymer.

A good deal is known about QCM devices. The military has experimented with them for years, using them to detect trace amounts of explosives and other hazardous compounds and measuring mass changes to a resolution of 1 pg. For example, 1 pg of methane in a 1 litre sample volume at s.t.p produces a methane concentration of 1.4 ppb. In addition QCM devices are remarkably linear over a wide dynamic range. Their response to water is dependent upon the absorbent materials employed and their sensitivity to changes in temperature can be made negligible.

Tailoring a QCM sensor for specific applications is done by adjusting its polymer coating. A large number of coatings are available. The response and recovery times of the resonant structure are minimised by reducing the size and mass of the quartz crystal along with the thickness of the polymer coating. Batch-to-batch variability is not a problem because these devices measure a normalised frequency change, a differential measurement that removes a common mode noise.

The SAW sensor differs from the QCM in several important ways. First, a Rayleigh wave travels over the surface of the device, not through its volume. SAW sensors operate at much higher frequencies and so can generate a larger change in frequency. A typical SAW device operates in the 100s of MHz region, but SAW devices can measure changes in mass to the same order of magnitude as QCM. Even though the frequency change is larger, increased surface to volume ratios mean that the signal to noise ratio is usually poorer. Hence, SAW devices can actually be less sensitive than QCM in some instances.

As with QCMs many polymer coatings are available for SAWs, and as with the other sensor types, differential measurements can eliminate mode effects. For example, two adjacent SAW devices on the same substrate can be operated as a differential pair to remove temperature variations and power line noise.

A disadvantage of both QCM and SAW sensors is their need for frequency detectors, whose resonant frequencies can drift as the active membrane ages.

Metal-oxide-silicon field effect transistor (MOSFET) are also used as odour sensing devices. These operate on the principle that VOCs in contact with a catalytic metal can produce a reaction in the metal.

The products of the reaction can diffuse through the gate of a MOSFET to change the electrical properties of the device. The sensitivity and selectivity of the devices can be optimised by varying the type and thickness of the metal catalyst and operating them at different temperature.

An advantage of MOSFET sensors is that they can be made with IC fabrication processes, so that batch-to-batch variations can be minimised. A disadvantage is that the catalysed reaction products, such as hydrogen, must penetrate the catalytic metallic layer in order to influence the charge at the channel. This means that the package must have a window to permit gas to interact with the gate structure on the IC chip. Thus it is important to maintain a hermetic seal for electrical connections to the chips. MOSFET sensors also undergo baseline drift similar to that of conductivity sensors. As before, this is a disadvantage.

Optical fibre sensors are also used as electronic nose sensors. These utilise glass fibres with a thin chemically active material coating on their sides or ends. A light source at a single frequency (or at a narrow band of frequencies) is used to interrogate the active material, which in turn responds with a change in colour to the presence of the VOCs to be detected and measured. The active material contains chemically active fluorescent dyes immobilised in an organic polymer matrix. As VOCs interact with it, the polarity of the fluorescent dyes is altered and they respond by shifting their fluorescent emission spectrum. When a pulse of light from an external source interrogates the sensor, the fluorescent dye responds by emitting light at a different frequency. As the source intensity is much greater than the sensor response, care must be taken to ensure that the response photodetectors are protected from the source emission.

A disadvantage of optical fibre sensors is that the instrumentation and control system is complex, which adds to fabrication costs. In addition, these sensors have a limited lifetime due to is photobleaching, where the fluorescent dyes are slowly consumed by the sensing process.

Many problems with existing electronic nose sensors exist. An object of the present invention is to provide a new method and sensor system for identifying gases.

According to one aspect of the present invention there is provided a method of identifying gases, the method involving forming a plasma using the gas to be identified, detecting light emitted from the plasma and using the detected light to identify the gas.

Each gas has a unique optical spectra, which can be used as a fingerprint to identify it. Hence, by generating a plasma and detecting optical emissions therefrom, an effective method of identifying a gas is provided. An advantage of this method is that it can be used with a wide variety of gases and requires no prior surface treatment of the plasma electrodes.

The method may further involve forming a plasma using a known gas, detecting light emitted from the known gas plasma and storing a spectra associated with the known gas. In this way, a library of spectra for known gases can be built up.

According to another aspect of the present invention there is provided a system for identifying gases, the system comprising means for forming a plasma using the gas to be identified, a detector for detecting light emitted from the plasma and a processor for using the detected light to identify the gas.

The system may further comprise a memory for storing a spectra associated with a known gas, which spectra can be used by the processor to identify the unknown gas.

The means for forming a plasma may comprise electrodes. The electrodes may be spaced apart by an amount in the range of substantially 40 to 200 µm, preferably 50 to 100 µm. The electrodes may be separated by a spacer. The electrodes may be excited by inductive coupling.

The electrodes may be provided as part of a spectrometer cell comprising opposing first and second substrates, the first substrate having a first array of electrodes and the second substrate having a second array of electrodes, which electrodes together define a sensor array of individually addressable elements. In a sense, each overlap between the first and second arrays of electrodes creates a series of "pixels" for individual excitation and thus use as a spectrometer sensor element.

The electrodes on each array may be linear. The electrode arrays may be located on internal cell-surfaces of the substrates. At least one of the substrates may be formed of material transparent to the relevant spectrometer wavelengths. At least one of the substrates may be wholly or substantially formed from glass. An advantage of this is that it can act as a light guide to allow the sensor signals to be guided to suitable, possibly distal, spectrometer detectors, possibly located along one or more edges of the glass substrates. At least one of the substrates may be wholly or substantially formed from silicon.

The electrodes may be formed of any suitable conductive material. The electrodes may be transparent. Suitable materials include tin oxide and titanium dioxide. Other materials include carbon, diamond-like carbon, nanotubes, onion rings any other form of fulerine or any coating that has a high field emission. This has the benefit of lowering the turn on potential (breakdown voltage). Alternatively, these materials could be used to coat tin oxide or titanium dioxide electrodes.

The use of a plurality of sensor elements allows one or more sensor element to be referenced as "calibration" elements able to provide a known calibration signal for simultaneous comparison with signal(s) received from the gas plasma being sampled. This overcomes the known difficulty that input conditions into any spectrometer always vary slightly, and indeed even "pure" calibration samples provide different spectra under even very slightly different conditions. Using a plurality of sensor elements also provides the ability to use statistical analysis to determine the average detected sample, which average should provide a better determination of the relevant portion of the gas sample than detection only by one sensor element. In addition, using a plurality of sensor elements, individual gas types can be referenced, such as a single element, e.g. hydrogen, or a molecule/compound such as acetone. Using a plurality of sensor elements also provides stability in use and self-error/ life testing. That is, the mis-function of any one single sensor element, or even its complete failure, should not affect a multiple detected signal. In addition, a new sensor element can immediately be brought into use upon failure of an existing element.

Various systems and methods in which the invention is embodied will now be described by way of example only and with reference to the accompanying drawings, of which:

FIG. 5 is a table showing identification results for five air, acetone and vinegar samples, which results were obtained using a first set of analysis criteria;

FIG. 6 is a table showing identification results for five air, acetone and vinegar samples, which results were obtained using a second set of analysis criteria;

FIG. 7 is a table showing identification results for ten air, acetone and vinegar samples, which results were obtained using a third set of analysis criteria;

FIG. 8 is a table showing identification results for two unknown samples A and B, which samples collected using a first method;

FIG. 9 is a table showing identification results for samples A and B, which samples were collected using another method;

Figure 1:
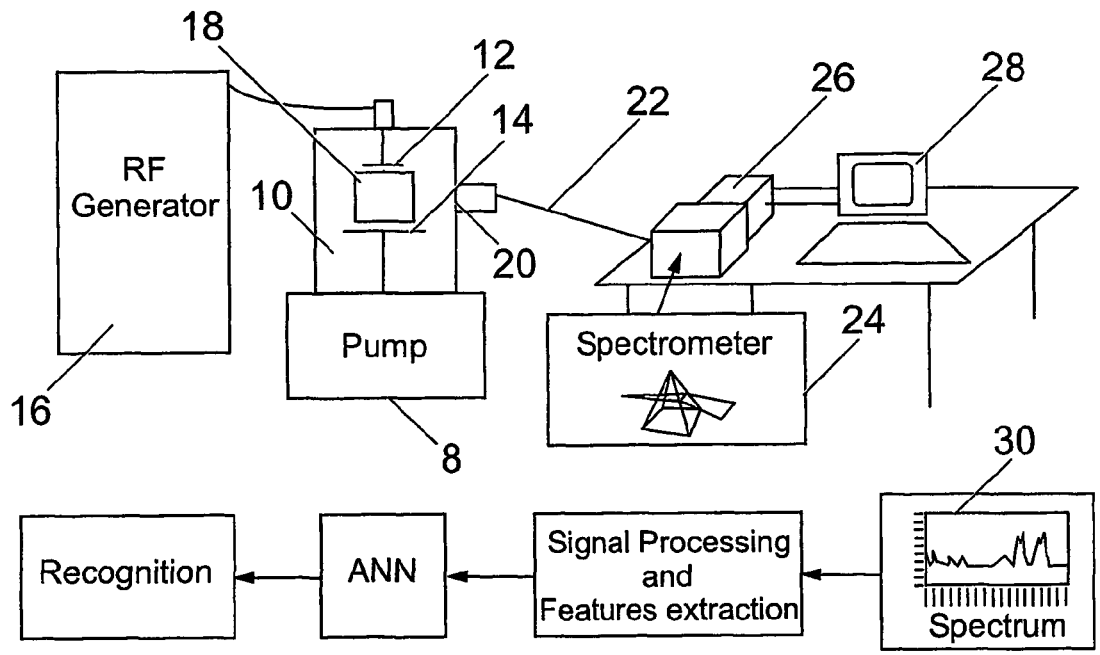
FIG. 1 is a block diagram of a first plasma optical emission spectroscope.

FIG. 1 shows an Edwards vacuum system 8, which has a vacuum chamber 10 that contains a parallel plate electrode having a top insulated driven electrode 12 and a lower grounded electrode 14. The top (driven) electrode 12 has a diameter of 4.5 cm and the grounded electrode 14 has a diameter of 21 cm. The distance between the electrodes 12 and 14 is 2 cm. Connected to the vacuum system is a Plasma Them 13.56 MHz r.f. generator 16 that has a power supply, which can be varied from 0 to 550W and includes an auto mode for automatic impedance matching to the load for reduction of power loss due to reflection. Gas is introduced into the vacuum chamber 10 and a plasma 18 is created using the generator 14. The plasma emits light that has an optical spectrum that is unique to the gas in the chamber 10.

Formed through a wall of the vacuum chamber 10 is a glass window 20, through which light generated by the plasma 18 can pass. This window 20 is adapted to filter out emission below 320 nm and above 950 nm. Optically connected to the glass window 20 is a fibre optic cable 22, which is used to feed light generated in the vacuum chamber into an Oriel MultiSpec 77400 spectrometer 24. This spectrometer has a 1200l/mm diffraction grating producing wavelength dispersion. A water cooled InstaSpec CCD array 26 is used to detect the incident wavelength intensity over 1024 pixels. Connected to the CCD array 26 is a computer 28, on which a spectra 30 of the detected light is displayed using Oriel Instaspec IV software. The spectra 30 is saved in ASCII format. The spectrometer allows a wavelength range of $\Delta\lambda=150$ nm to be detected simultaneously on the CCD.

Figure 2:
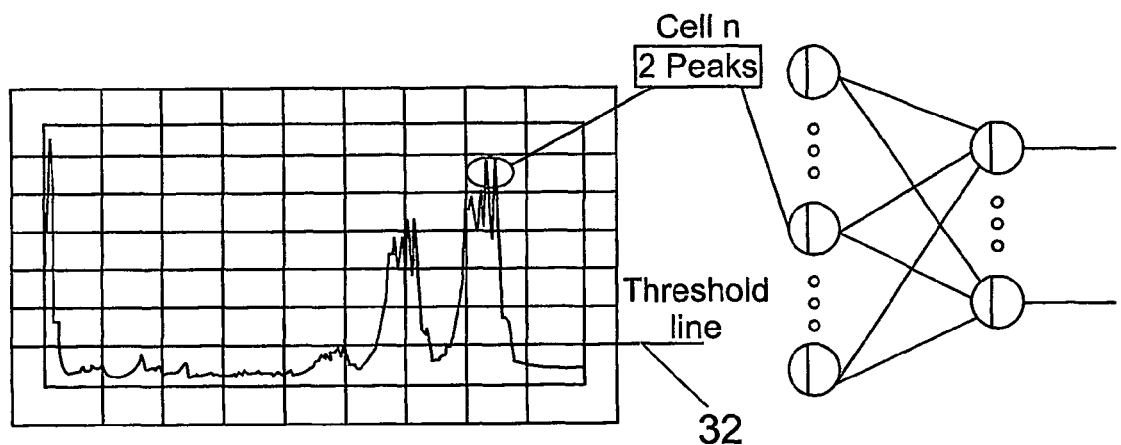
FIG. 2 illustrates steps of an analysis process.

Signal processing of the spectrum is performed by importing the ASCII file of the spectrum into National Instruments LabView program and splitting the spectrum up into regions as shown in FIG. 2. If this subdivision is performed, a grid is built on the spectrum. The final result is the creation of cells, inside which peaks can be counted. A feature can be expressed as 'feature X is the number of peaks in cell X'. Also, a threshold 32 can be set in order to ignore low cells containing noise peaks. The algorithm for a single spectrum can be briefly summarised in the following steps: (1) initial to 0 the number of peaks for each cell; (2) detect peaks; (3) for each peak, determine its array position and add 1 to the number of peaks determined to lie in that cell. Ultimately, each cell/feature has a corresponding input in an artificial neural network (ANN) and its value can be fed in. It should be noted that cell dimension controls give a large flexibility for the grid resolution. The resolution can be adapted to the needs of the application, ranging between a grid solely formed by columns and a grid with just rows. Extreme grid configurations could be very useful in specific applications.

ANNs can be based on several theories and consequently several network types exist. Within each network type many variants can be achieved by changing specific parameters. Disregarding the type and architecture, any artificial NN can be simulated on a PC or workstation. Custom programs can be coded or otherwise simulation software can be used. In any case, the simulation should provide an interface to feed in the input valves and to observe the outputs. In the example of FIG. 1, the simulation software chosen was NeuralWorks Professional II/Plus© developed by NeuralWare Inc. This is a back-propagation network with a learning Delta Rule which uses a Sigmoid activation function. A valve of 0.05 has been considered for the Momentum and 0.1 for LCoef Ratio, the other NN values being set to their default values.

Figures 3, 4:
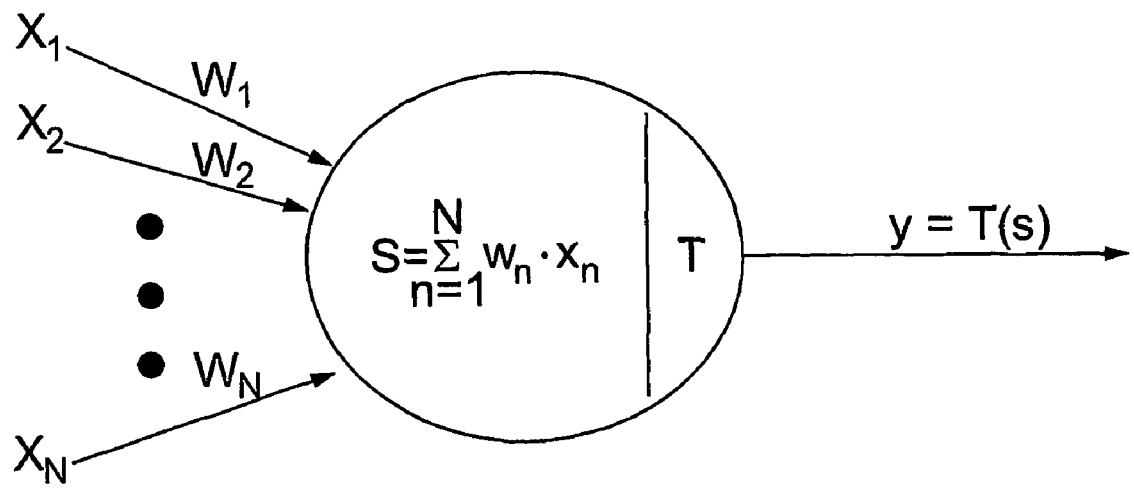
FIG. 3 is a diagrammatic representation of a perceptron, which is used in the analysis of spectra collected using the spectroscope of FIG. 1.
FIG. 4 is a table showing identification results for five air and nitrogen samples.

The fundamental element of an NN is the Perceptron. A perceptron is a node with N inputs $x_1$ to $x_N$ and one output, y, as shown in FIG. 3. The inputs are multiplied by adjustable weights ($w_1, \ldots, w_N$) and then summed together. The sum s obtained is the argument of a function called the threshold function or activation function T. The features vector $x=(x_1, \ldots x_N)$, can be fed into the perceptron. Then, the activation function T acts on the sum s. T can be a simple step function which has value 1 for s greater than a certain value and 0 for smaller values. More complex activation functions are possible. The resulting effect of a perceptron is to linearly divide the features space in two half-space. However, the activation function determines the division of the feature space.

In order to increase the power of the perceptron, it is possible to pull perceptrons in a layer. If M is the number of the perceptrons in the layer, it is possible to divide the space in 2M half-space or up to $2^M$ convex regions with a minimum of M+1 convex regions. In order to increase further the power of an ANN, it is possible to consider Multiple-Layered Perceptrons where the M output of the first layer will become the inputs of the second layer and so on. In these cases, the layers whose outputs are fed into another layer are called hidden layers. A multiple-layered NN can non-linearly divide the features space.

If the activation function is a unitary step function, then, feeding a features vector to the network, returns a vector which represents the belonging class. If, alternatively, the activation function is more complex, the output vector will be mapped in the space of the classes end and it will be necessary to do a distance evaluation to determine the belonging class. Theoretically, with a single hidden layer, it is possible to perform any kind of analysis that would be possible with more layers. Nevertheless, multiple hidden layers can be used to avoid a large number of perceptrons in a single layer. Until now, a general form of an NN has been discussed, which can be called a Feed-forward NN. Changing the available parameters, it is possible to obtain several different NN which would suit many different applications. The available parameters are the number of perceptrons, layers, the values of the weights and the shapes of the activation functions for each layer. Moreover, an algorithm called Functional Link Nets can provide a single layer network of extra dimensions or extra features in order to distinguish classes non-linearly sepearable.

Initially, NNs need to be trained (supervised or unsupervised). When a set of patterns is available, it is possible to adjust the weights in order to have the desired classes as outputs and the several available algorithms to perform this task give a wide range of options. In the case of clustering, there exist also many algorithms which are able to automatically adjust the weights.

ANNs are not the only solution in associative mappings. Interesting results can be also obtained using Fuzzy approaches. Fuzzy Logic can also offer decision-theoretic solution to pattern recognition problems. Fuzzy logic will not be here discussed but it is important to know the existence of the possible options in pattern recognition. A fuller explanation of fuzzy logic is given in the article 'Pattern recognition with fuzzy objective function algorithms' by BEZDEK, J. C, (Plentum, 1981).

When the system of FIG. 1 is used, the chamber 10 is evacuated to a base pressure of $10^{-7}$ mbar. Gases are fed into the chamber 10 using a needle valve (not shown) from either a pressurised vessel, a heated U-tube, or by direct diffusion of the volatile compounds from the container. The Plasma Therm generator 16 is used to generate a plasma 18, the r.f. power being set at 10W. During plasma generation, a high vacuum baffle valve is employed in order to maintain a constant pressure of $10^{-3}$ mbar. Light emitted by the plasma 18 passes through the glass window 20 and is detected by the Spectrometer 24. The resultant spectra 30 is shown on the computer screen and analysed using the ANN techniques described previously. When the gas introduced into the plasma chamber is a known gas, the system is taught to recognise this gas by storing known spectra or analysis data, together with details of the gas. In this way, the apparatus is trained or calibrated. When the gas introduced into the plasma chamber is an unknown gas, the system is adapted to compare the spectra or data that results from the generation of the plasma 18 with the stored values, thereby to identify the gas.

The system of FIG. 1 can be used to detect or identify many different gases. A variety of gases and gas mixtures have been tested.

Recognition of Air/Nitrogen

In this case, for the analysis of the spectra, the grid resolution was set to 100 pixels (X)*0.2 normalised intensity (Y) for feature extraction. The neural network was configured using hidden layer 1 of 25 perceptrons, (or processing elements, PE's) and hidden layer 2 of 10 PE's, 55 inputs were used. The training or teaching phase was performed using data from the first 10 spectra of air and the first 10 spectra of nitrogen, thereby to teach the system to recognise spectra for air and nitrogen respectively.

FIG. 4 shows the results obtained testing 5 samples of air and 5 of nitrogen. For each sample, four consecutive spectra were considered with central wavelengths of respectively 400 nm, 550 nm, 700 nm and 850 nm. The spectra supplied 1024×4=4096 intensities (some of which overlap). The output of 1 or 0 indicates the relative certainty of the program to the presence or absence of the gas in question. It can be seen that recognition was performed accurately. It should be noted that the system distinguished the gases with only 55 inputs.

The same procedure above, was also executed reducing the number of PE's in the Hidden layers. In particular, 0 PE's have been used for both hidden layers obtaining the same results and demonstrating the effectiveness of the feature extraction process. It can be seen, therefore, that the arrangement of FIG. 1 is effective for detecting air and nitrogen accurately.

Recognition of Air/Acetone/Vinegar

As another example, the arrangement of FIG. 1 was used to detect one spectrum of acetone, one of air and one of vinegar. This procedure was repeated 15 times for a total of 45 spectra. Air spectra were acquired as described above. Acetone and vinegar, however, had to be evaporated and for this purpose two U tubes (not shown) were used, one for acetone and the other for vinegar. A rubber pipe was connected from the U tube to the needle valve and the evaporation of vinegar or acetone was facilitated by heating and the consequent spectrum could be recorded. Between any two acquisitions the chamber pressure was brought below $10^{-6}$ mbar.

As can be seen in FIG. 5, acetone and vinegar were recognised, but air was confused twice with vinegar (the second and the third sample of air). Nevertheless, these outputs are promising as 13 out of 15 samples were correctly recognised. It is expected that a wider set of training samples would improve the prediction accuracy.

Effect of Hidden Layers

The effect of reducing hidden layer PE's was investigated by reducing the PE's in both hidden layers to 0 and keeping the same number of inputs. In this case, the learning process was as successful as in the case with hidden layers, but slight differences could be seen in the results of the testing phase. The results of the process, when the hidden layers were reduced to 0 are shown in FIG. 6.

From FIG. 6 it can be seen that acetone and vinegar could still be recognised. However, differences can be seen in the first three samples of air when compared with the results of FIG. 5. The first has been recognised but its value has decreased (in the first column of the actual outputs). Also the second and third values have changed but, as in the previous procedure, they have been wrongly classified. Even if the differences are minimal, they could be noticed. With a larger training set, the differences would have been emphasised. It can be concluded that better results are obtained from the network with hidden layers (198 inputs-100PE's-50PE's).

Effect of Overloading

The risk of overloading the system with an excessive number of features was addressed. This effect can occur if the number of features is too large in relation with the number of training samples. Only 30 samples were considered for training in this experimental session and the risk of overloading is possible. A configuration such as a very high grid resolution could lead to an excessive number of cells/inputs. If this situation occurs, the ANN might be able to detect peculiar characteristics for any single sample and therefore it would be able to perfectly classify the samples in any desired set of classes.

FIG. 7 shows the classification of a misleading training. In this case, the NN was trained giving desired outputs which did not correspond to the samples. For example, the first three air samples were trained with the three different possible outputs (001 010 100). Classification could not be done properly. For instance, the first air sample was classified with very confusing values (0.2; 0.4; 0 instead of 0; 0; 1). Other rows show similar confusing results. This means that classification could not be easily performed for this set of classes, excluding the possibility of overload.

Recognition of Coffee Beans

The apparatus of FIG. 1 was used to distinguish between two types of coffee beans. In this case, the grid resolution was set to 100*0.05 for feature extraction and the neural network was configured using hidden layer 1 of 100 PE's and hidden layer 2 of 50 PE's. 198 inputs were used.

For this experimental session, two different blends of coffee were used—sample A and sample B, each of which was purchased from two different suppliers. Evaporation and acquisition were performed to provide a gas in the same way as in the case of vinegar and acetone. Training was completed successfully with the classification of all 16 samples.

FIG. 8 shows the results of the sample identification. From this it can be seen that the recognition is poor. However, the number of cells and the number of PE's in the hidden layer appeared sufficient. It was suspected that the reason for the unsuccessful results lay in the acquisition procedure, which is affected by the difficulties encountered in evaporating the coffee. To test this assumption the U tube evaporation system was discarded and odour was acquired from the beans by passing a tube directly into the coffee container. Using the modified collection technique, no problems were encountered in the classification of the 30 samples of the two different blends. Results after testing are listed in FIG. 9, which shows that 9 out of 10 samples were correctly recognised.

Figure 10:
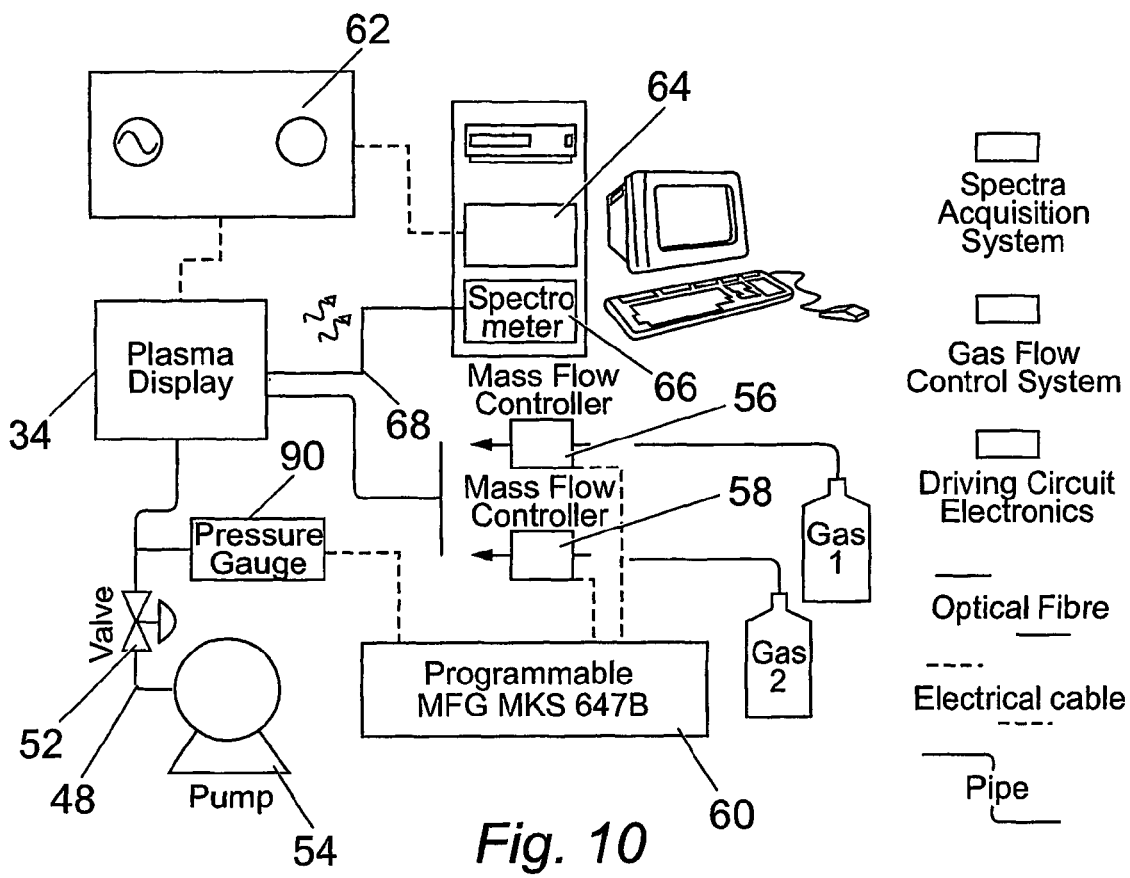
FIG. 10 is a block diagram of another plasma optical emission spectroscope.

FIG. 10 shows another system that can be used for recognising gases. The overall system can be subdivided in four main subsystems: a plasma display 34, a gas flow control system, driving circuit electronics and a spectra acquisition system.

Figure 11:
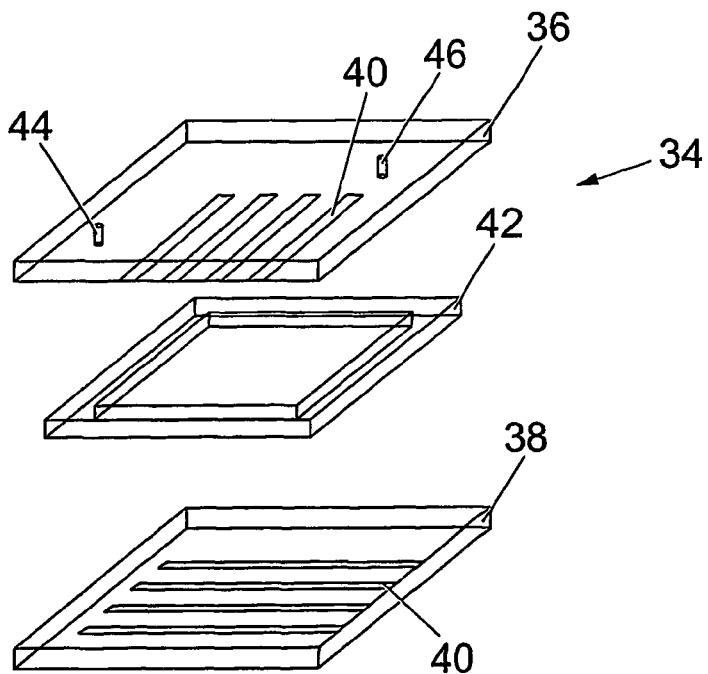
FIG. 11 is an exploded view of the constituent parts of a sensor that is used in the spectroscope of FIG. 10.

FIG. 11 shows the various parts of the plasma display 34. This is fabricated using a photolithography process. The plasma display 34 has two glass plates 36 and 38 that are patterned with tin oxide strips 40, which strips 40 form the plasma electrodes. The glass plates 36 and 38 are positioned so that the tin oxide strips 40 face inwardly towards each other. On each plate 36 and 38 are provided four electrode strips 40. The intersection point between the strips define pixels. Hence, in the display of FIG. 11, sixteen pixels are present. The voltage can be applied to each single electrode line so that the desired pixel is 'switched on'. A spacer 42 separates the two glass plates 36 and 38. The spacer 42 may be a film of teflon or a soft silicon rubber with some vacuum glue on each side or any other suitable material. The spacing between the inner faces of the glass plates is in the range of substantially 40 to 200 μm, preferably 50 to 100 μm. Two holes 44 and 46 are drilled in the top glass for the gas inlet 44 and outlet 46. As an alternative, the glass plates could be replaced by Si and the tin oxide electrodes could be replaced by doped silicon. In this case, the plasma display could be fabricated as a MEMS type-device.

Connected to the gas outlet of the plasma display is a pump, which pump is part of the gas flow control system. The gas flow control system has a pipe line from the plasma display 34 towards the pump, on which pipe line 48 are provided a pressure gauge 50 and a valve 52. The pressure gauge 50 is a Baratron® capacitance manometer type 626 purchased from MKS. It has a full-scale range of 1000 mmHg with an accuracy of 0.25% of reading. The valve 52 is needed to control the output flow to a pump 54 so that the desired pressure can be maintained. The pump 54 is a combination in series of a rotary pump and a diffusion pump. The gas inlet 44 of the display 34 is connected to two mass flow controllers 56 and 58, which regulate the mass and concentration of two different gases. A multichannel gas flow and pressure controller 60 controls the two mass flow controllers 56 and 58 and reads the pressure from the Baratron® manometer 50. This device allows flow set points and gas concentrations to be entered, which will be kept automatically as well as many other functions.

In order to drive the plasma display 34 to generate a plasma, a driving circuit 62 is provided. This can supply a voltage in the range of 0-700 Volts DC.

When connected to a signal generator, the drive circuit can deliver AC signals oscillating in the rang −300 to 300 Volts. It can control separately all eight electrode strips and connect in series variable resistors (0-10M) to provide current limiting. HM 2000 has a PC interface and a LabView® program, which together allow the measurement of voltage applied, voltage at the display electrodes, and current. The voltage applied is controllable either from the front panel of the HM 2000 or from PC. A provisional DAQ card 64 is used which has no output so that the voltage applied has to be controlled manually.

When a plasma is generated, light is emitted, which light it transmitted via an optical fibre to a spectrometer 66, which is a PC1000 PC Plug-in Spectrometer 66 by Ocean Optics. This is a miniature spectrometer 66 that fits in standard ISA-bus slot of a PC. It has spectral range of 350-850 nm and a blaze wavelength at 500 nm. Software is provided together with the spectrometer 66, OOIBase. OOIBase acquires data and performs basic operation such as background functions removal and integration. Some other functions such as smoothing are also possible. The spectrometer 66 should be self calibrated nevertheless some line shift may be present. An additional calibration has been performed with a helium neon laser.

In use of the system of FIG. 10, a gas that is to be recognised is introduced into the plasma display via the gas inlet. Gas introduced in this way moves between the glass plates 36 and 38 and the spacer 42. A voltage is then applied to the electrodes 40 in order to generate a plasma 18. Once the plasma is generated, light having a unique spectra is emitted. The glass plates in effect act as waveguides and guide the emitted light to an optical fibre from there to the spectrometer 66. As with the arrangement of FIG. 1, the spectrometer 66 is adapted to analyse the light received, thereby to assist in the identification of the gas.

Recognition of Acetone

Acetone was enclosed in a glass U-jar and the opening attached to the inlet of one of the two mass flow controllers 56 and 58. The other mass flow controller was connected to Argon bottle. Acetone mixed with air was flowing at 20 sccm and Argon at 0.8 sccm to maintain a pressure around 20.8 Torr. Argon was necessary to ease the discharge. A voltage of 610 Volts was applied across the electrodes 40. Spectra were then taken from the consequent emission. Another set of spectra was taken simply placing the mass flow controller inlet at the mouth of an acetone jar. In this case the inlet pipe was free to sample also air in the surrounding area. The third set of spectra was taken from plasma emission of air. Spectra were normalised by energy content before comparing them.

The most evident difference is shown around 383.69 nm. Some other peaks due to air elements hide peaks related to acetone (matrix effect). Nevertheless, detection of acetone odour is still possible.

Differences between closed-jar sampling and open-jar sampling suggest quantification capabilities. These results highlight the possibility of using such a simple technique to diagnose pathologies that undergo overproduction of acetone in body fluids (e.g. respiration gases). Large improvements can be obtained by varying spectral ranges and spectral resolution and adopting chemometric techniques.

The ability of the arrangement of FIGS. 1 and 10 to recognise gases has many useful applications. For example, in medicine, it is known that respiration gases from asthmatic patients differ from those of healthy adults. By detecting differences in the gases breathed out by a person, it is therefore possible to identify whether or not a person is asthmatic.

Asthma Diagnosis

Figure 12:
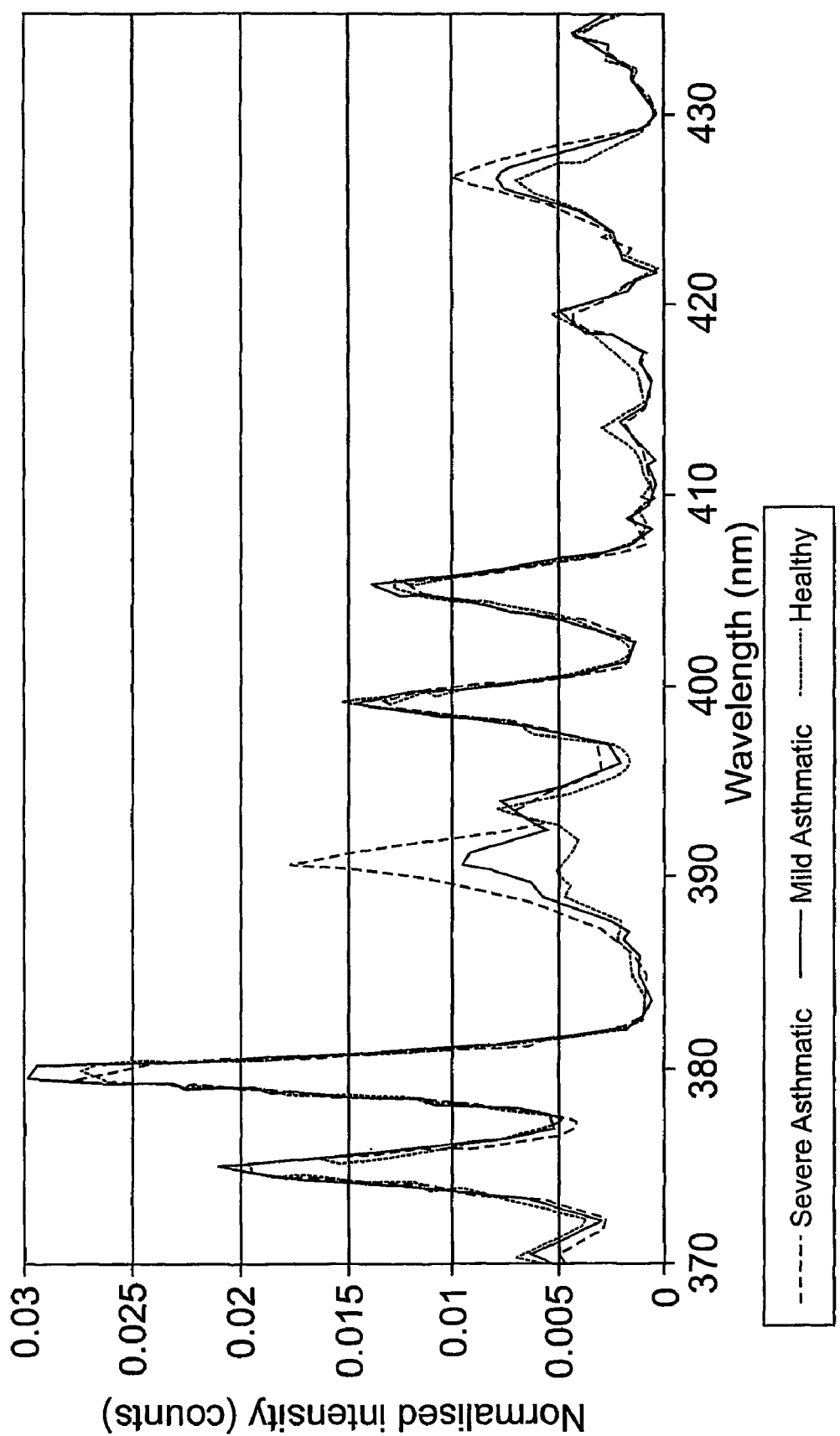
FIG. 12 shows various spectrum for a sample analysed using the system of FIG. 10.

Asthmatic subjects and healthy subjects were asked to breathe in balloons. In this manner respiration gases were then conveyed into the micro chamber through the mass flow controller. Flow rate was set to 0.8 sccm for Argon and 20 sccm for breathe samples. Initially, sets of respiration gases were taken from one severe asthmatic patient, a mild asthmatic patient and a health subject. Spectral emissions shown in FIG. 12. Differences are clearly shown by the spectra, suggesting that this may be a promising diagnosis tool.

A system has been developed based on plasma optical emission and an artificial neural network for the detection and recognition of gases. The system can distinguish species with similar chemical composition such as acetone and vinegar, and between different brands of coffee granules. The accuracy of the system depends upon the number of training samples fed into the neural network, the configuration of the network (PE's hidden layers) and the resolution of the grid used for feature extraction. However, even with relatively few training samples and little manipulation of the neural net the accuracy of the identification routine is still good. A further advantage is that the system is works reliably.

A skilled person will appreciate that variations of the disclosed arrangements are possible without departing from the invention. Accordingly, the above description of specific embodiments is made by way of example only and not for the purposes of limitation. In particular, it will be clear to the skilled person that minor modifications can be made without significant changes to the devices and methods described above.

The invention claimed is:

1. A system for identifying gases, the system comprising means for forming a plasma using the gas to be identified, a sensor for sensing light emitted from the plasma and a processor adapted to use information on the sensed light to identify the gas, wherein the means for forming a plasma comprises electrodes which are provided as part of a cell, wherein the cell comprises opposing first and second substrates, a region between the first and second substrates, the first substrate has a first array of electrodes adjacent the region and the second substrate has a second array of electrodes adjacent the region, which electrodes together define an array of individually addressable elements, individually operable to form a plasma in the region.

2. A system as claimed in claim 1, in which at least one of the substrates is operable to act as a waveguide for light emitted by the plasma.

3. A system as claimed in claim 1, wherein the electrodes on each array are linear.

4. A system as claimed in claim 1, wherein the electrode arrays are located on internal cell-surfaces of the substrates.

5. A system as claimed in claim 1, wherein at least one of the substrates is formed of material transparent to relevant spectrometer wavelengths.

6. A system as claimed in claim 1, wherein at least one of the substrates is wholly or substantially formed from glass.

7. A system as claimed in claim 1, wherein the electrodes are spaced apart by an amount in the range of 40 to 200 µm.

8. A system as claimed in claim 1, wherein the electrodes are separated by a gasket.

9. A system as claimed in claim 1, wherein the electrodes are excited by inductive coupling.

10. A system as claimed in claim 1, comprising a memory for storing a spectra or data associated with a known gas, which spectra or data is used by the processor to identify the gas.

11. A system as claimed in claim 10, wherein at least one of the substrates is operable to act as a waveguide for light emitted by the plasma.

12. A system as claimed in claim 10, wherein the electrodes on each array are linear.

13. A system as claimed in claim 10, wherein the electrode arrays are located on internal cell-surfaces of the substrates.

14. A system as claimed in claim 10, wherein at least one of the substrates is formed of material transparent to relevant spectrometer wavelengths.

15. A system as claimed in claim 10, wherein at least one of the substrates is wholly or substantially formed from glass.

16. A system as claimed in claim 10, wherein the electrodes are spaced apart by an amount in the range of 40 to 200 µm.

17. A system as claimed in claim 10, wherein the electrodes are separated by a gasket.

18. A system as claimed in claim 1, wherein the electrodes are spaced apart by an amount in the range of substantially 50 to 100 µm.

19. A method of identifying gases, the method involving forming a plasma using the gas to be identified, sensing light emitted from the plasma and using the sensed light to identify the gas, wherein the step of forming a plasma includes providing electrodes as part of the cell, wherein the cell comprises opposing first and second substrates, a region between the first and second substrates, the first substrate has a first array of electrodes adjacent the region and the second substrate has a second array of electrodes adjacent the region, which electrodes together define an array of individually addressable elements, individually operable to form a plasma in the region.

20. A method as claimed in claim 19 further involving forming a plasma using a known gas, sensing light emitted from the known gas plasma and storing a spectra associated with the known gas.

* * * * *